(12) United States Patent
Amis et al.

(10) Patent No.: US 7,104,994 B1
(45) Date of Patent: Sep. 12, 2006

(54) HEATING PEN, TACK SEATING DEVICE, AND TAP AND SURGICAL IMPLANTATION METHODS USING SAME

(75) Inventors: James Peter Amis, Carlsbad, CA (US); Christopher J. Calhoun, San Diego, CA (US)

(73) Assignee: Cytori Therapeutics, Inc., San Diego, CA (US)

( * ) Notice: Subject to any disclaimer, the term of this patent is extended or adjusted under 35 U.S.C. 154(b) by 602 days.

(21) Appl. No.: 10/110,161

(22) PCT Filed: Oct. 5, 2000

(86) PCT No.: PCT/US00/27627

§ 371 (c)(1),
(2), (4) Date: Sep. 3, 2002

(87) PCT Pub. No.: WO01/24844

PCT Pub. Date: Apr. 12, 2001

Related U.S. Application Data

(60) Provisional application No. 60/157,825, filed on Oct. 5, 1999.

(51) Int. Cl.
*A61B 17/58* (2006.01)
*H05B 1/00* (2006.01)

(52) U.S. Cl. .................. 606/69; 606/104; 219/229

(58) Field of Classification Search ............ 606/69–71, 606/75, 77, 104; 227/146, 140, 147, 148; 219/229, 236, 233; 408/215–217; 81/455; 433/32

See application file for complete search history.

(56) References Cited

U.S. PATENT DOCUMENTS

| | | | |
|---|---|---|---|
| 274,492 A | 3/1883 | Harvey | |
| 2,325,627 A | 8/1943 | Neilson | |
| 3,558,854 A | 1/1971 | Siegel | |
| 3,821,513 A | 6/1974 | Christensen | |
| 3,901,298 A * | 8/1975 | Eby | 81/455 |
| 5,073,696 A * | 12/1991 | Patillo et al. | 219/233 |
| 5,374,188 A * | 12/1994 | Frank et al. | 433/32 |
| 5,398,861 A | 3/1995 | Green | |
| 5,451,224 A | 9/1995 | Goble et al. | |
| 5,544,552 A | 8/1996 | Kirsch et al. | |
| 5,741,268 A | 4/1998 | Schutz | |
| 5,779,706 A | 7/1998 | Tschakaloff | |

OTHER PUBLICATIONS

P.C.T. International Search Report, Apr. 9, 2001.

* cited by examiner

*Primary Examiner*—Julian W. Woo
(74) *Attorney, Agent, or Firm*—Stout, Uxa, Buyan & Mullins, LLP

(57) ABSTRACT

A method, apparatus and system for applying bio-resorbable membranes or plates to bone for internal fixation of bone defects is disclosed.

25 Claims, 10 Drawing Sheets

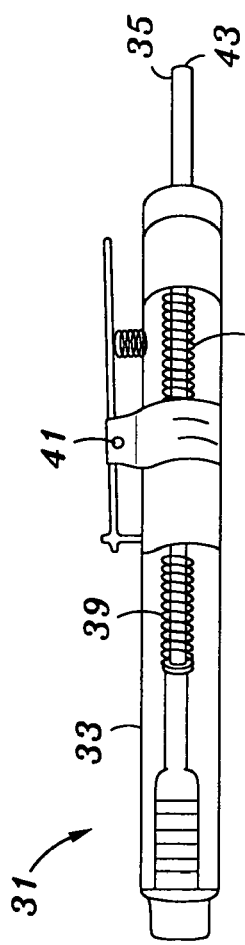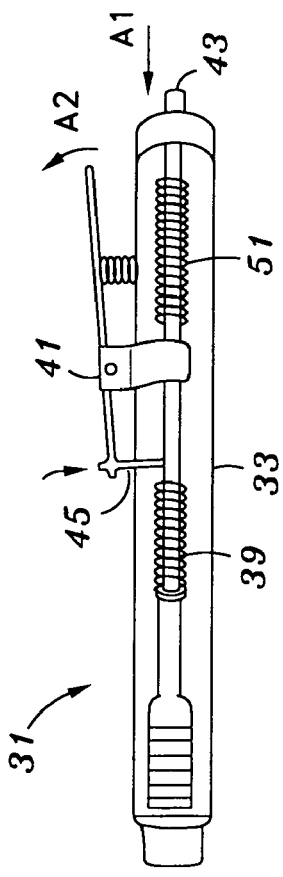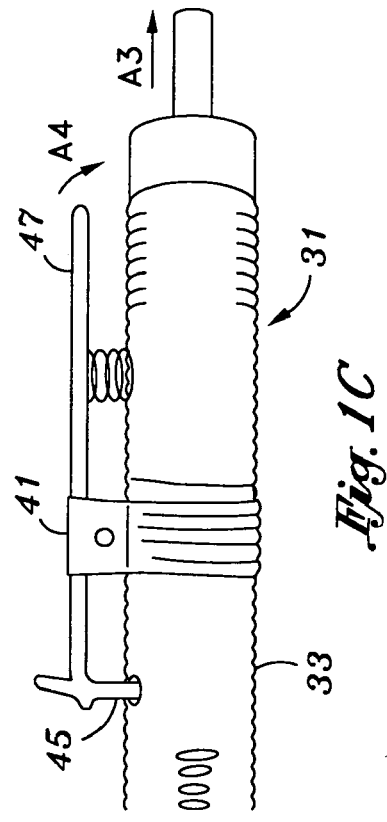

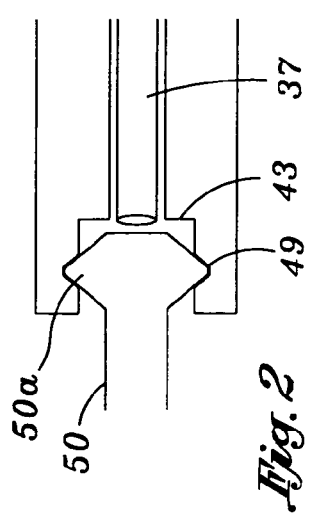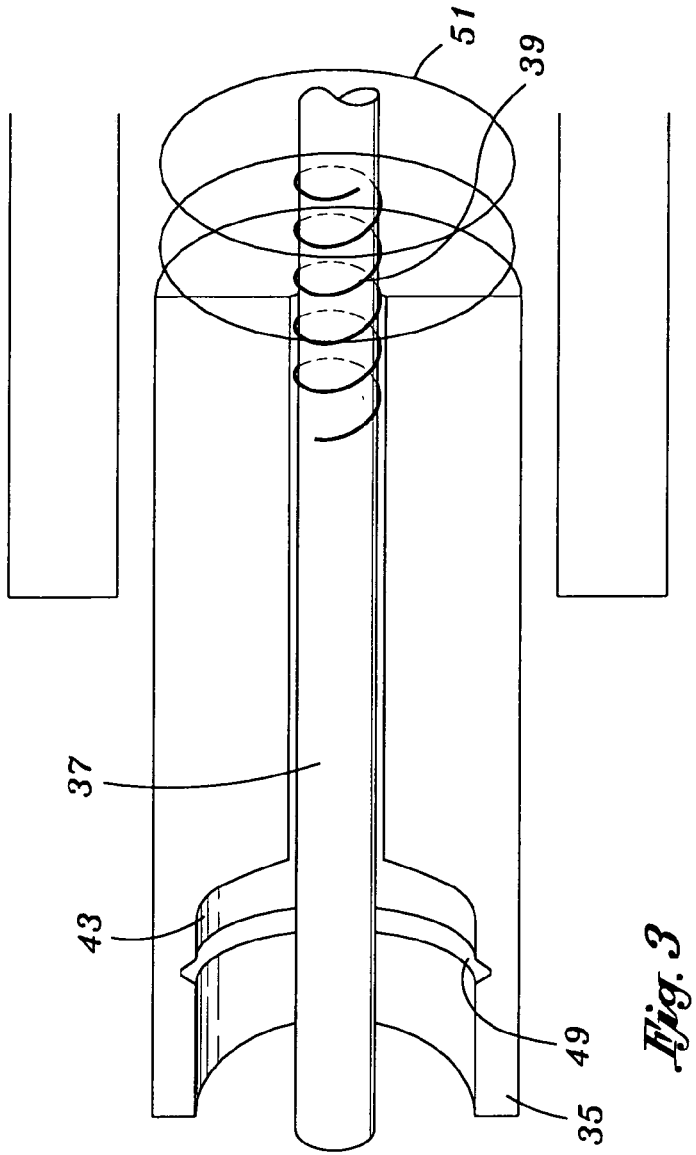

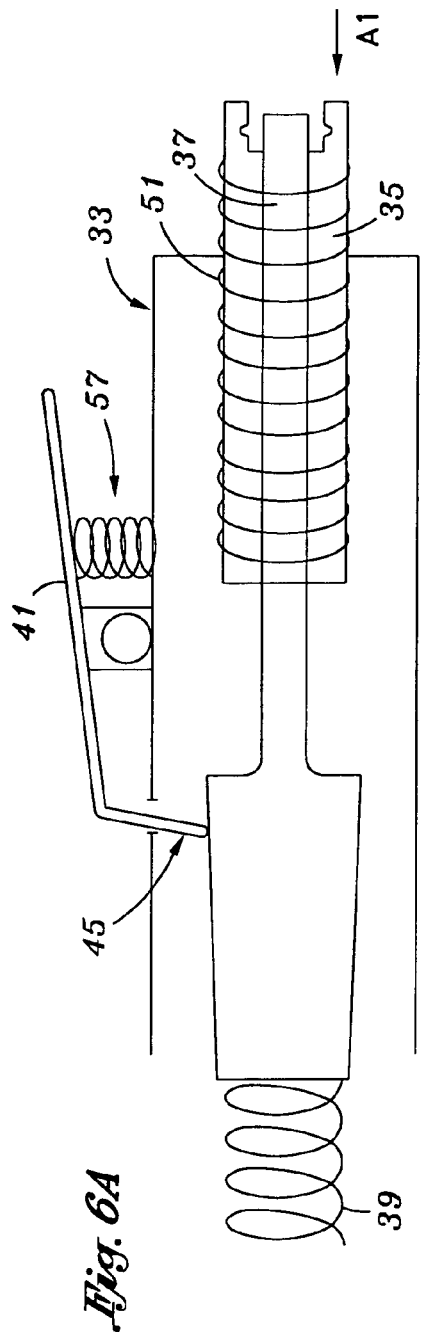
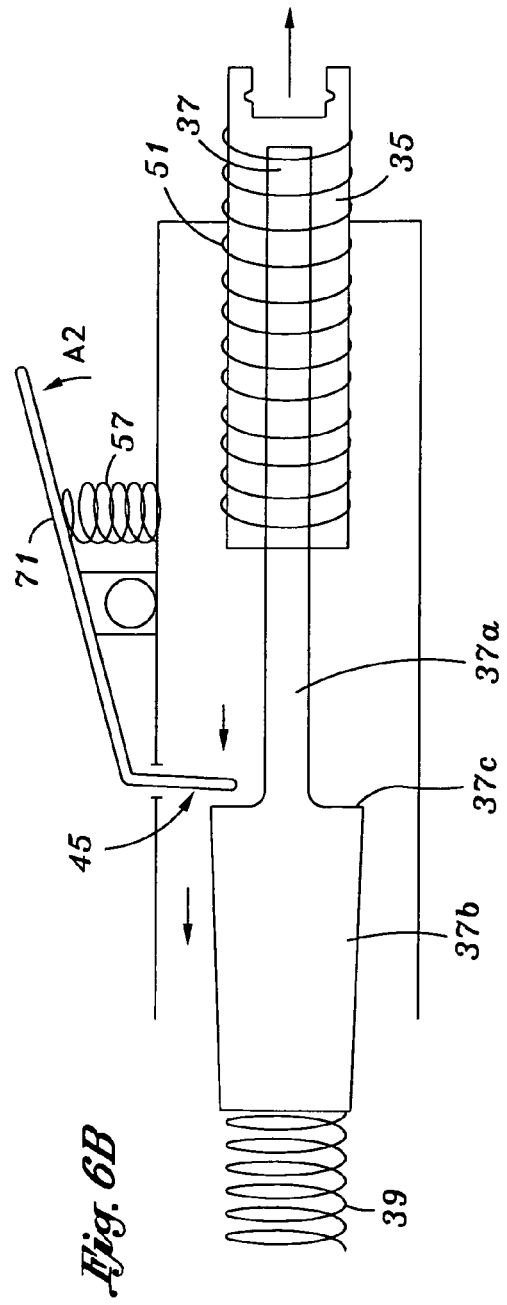
Fig. 6A
Fig. 6B

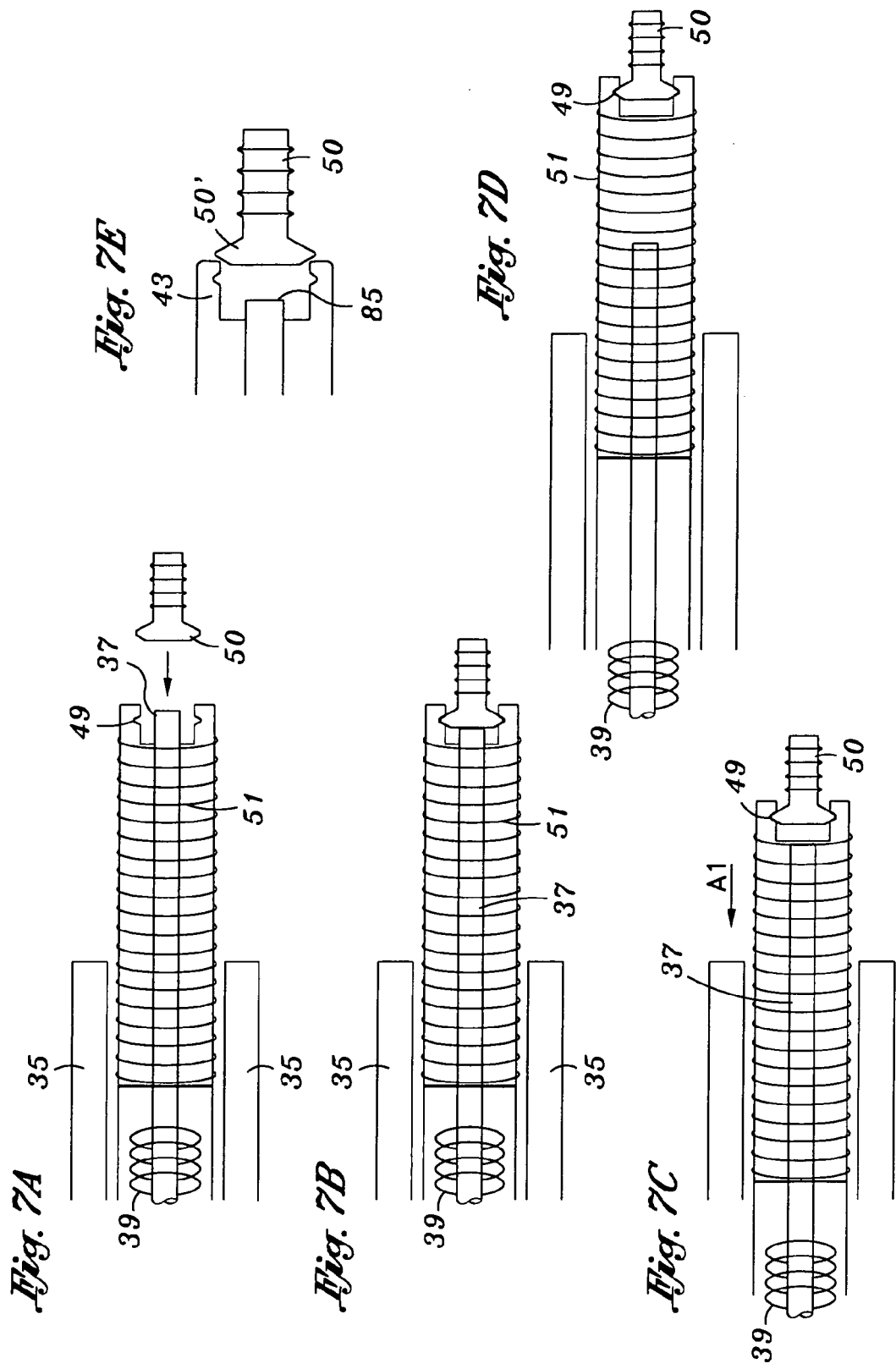

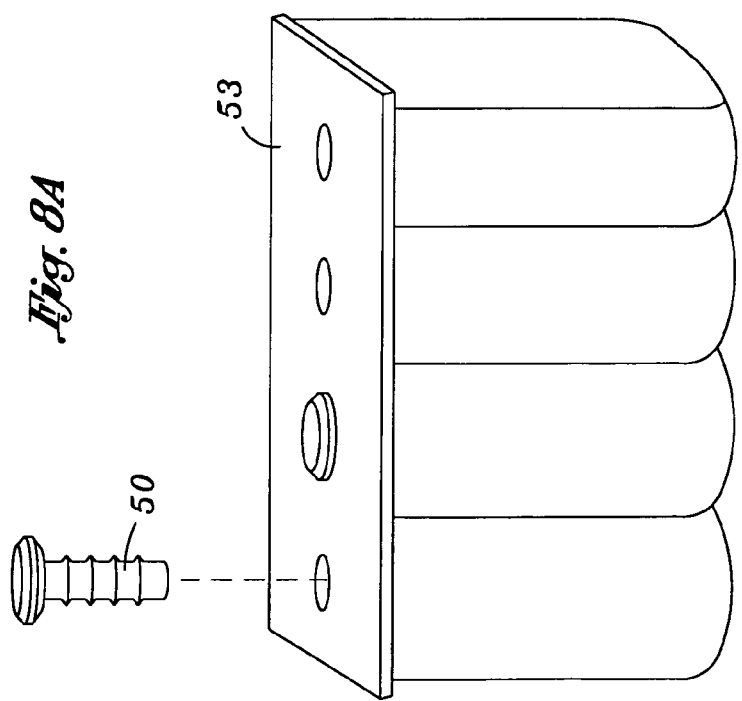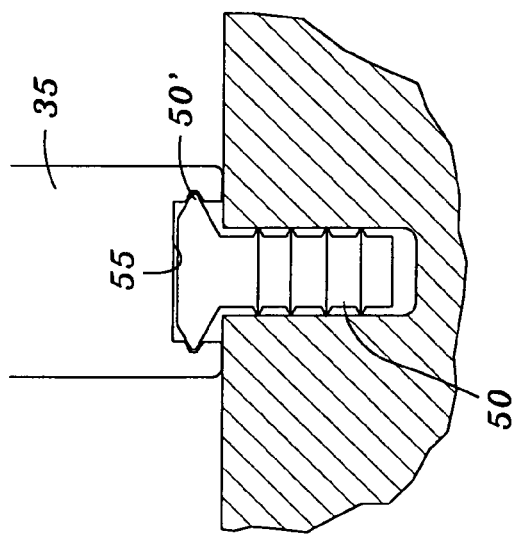

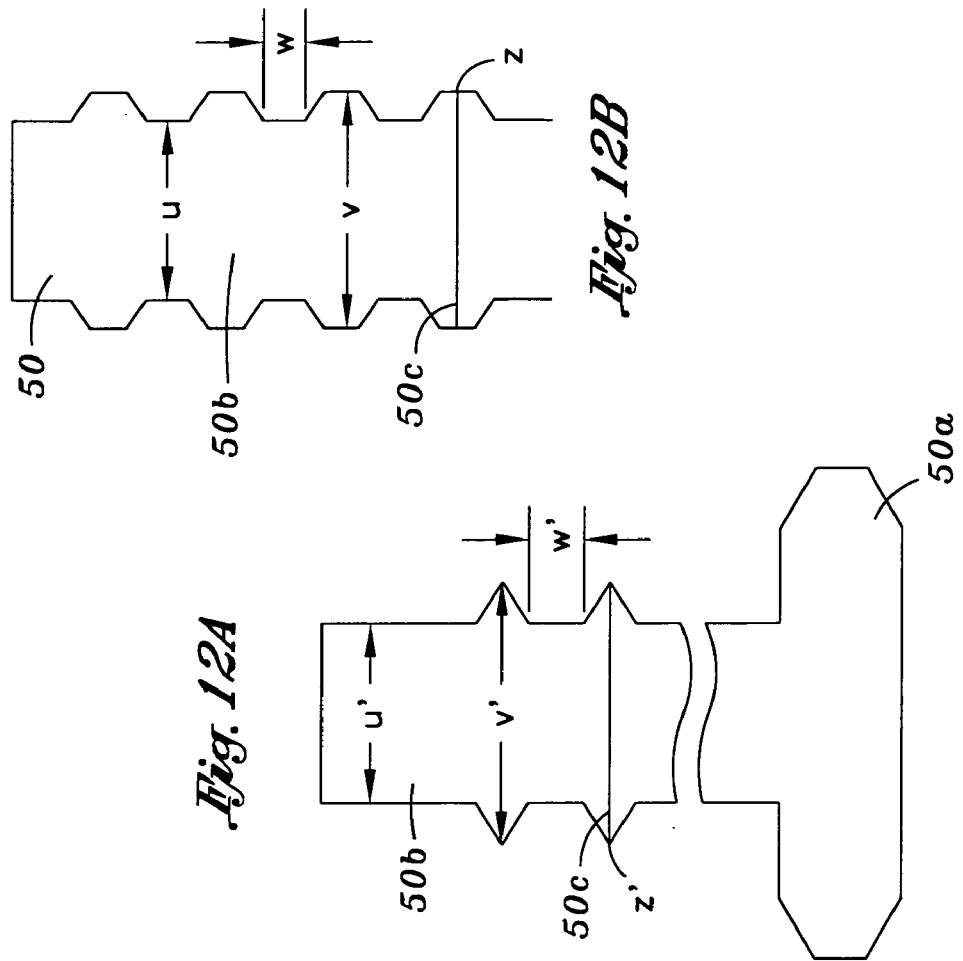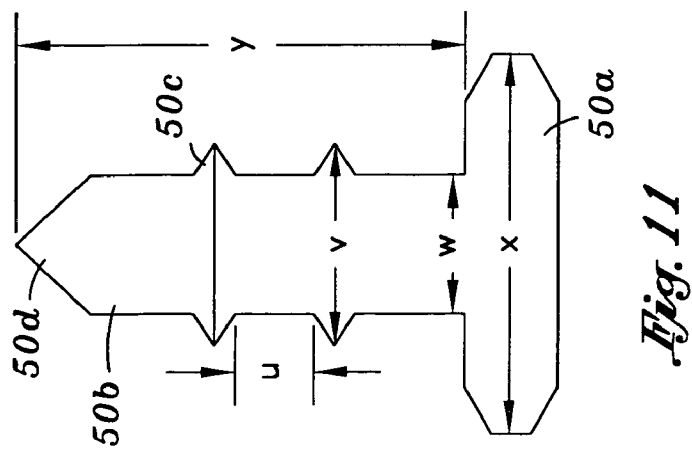

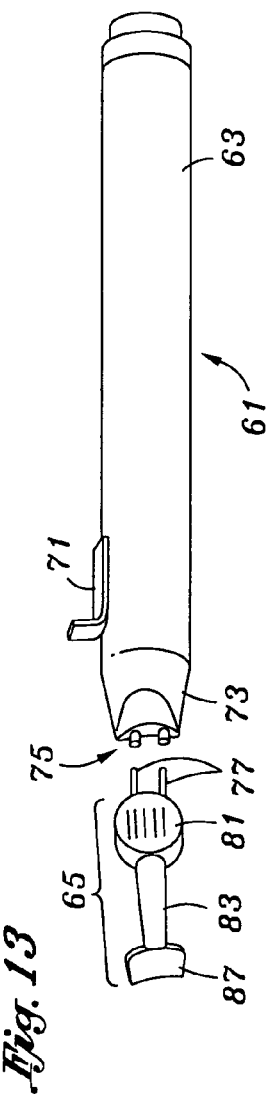
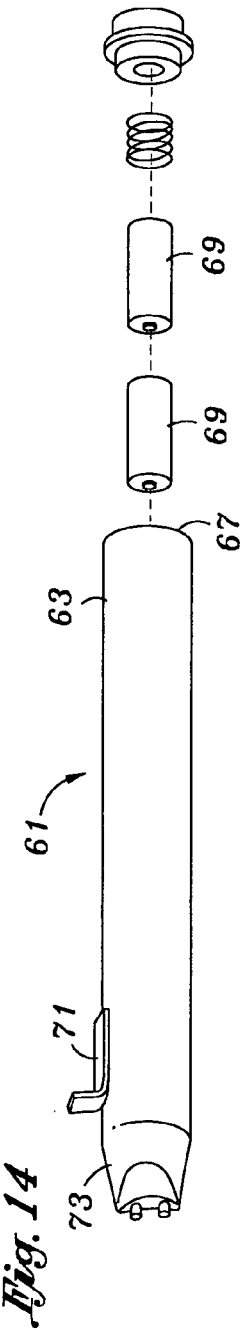
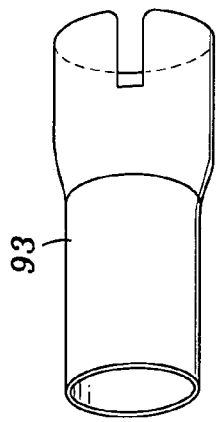
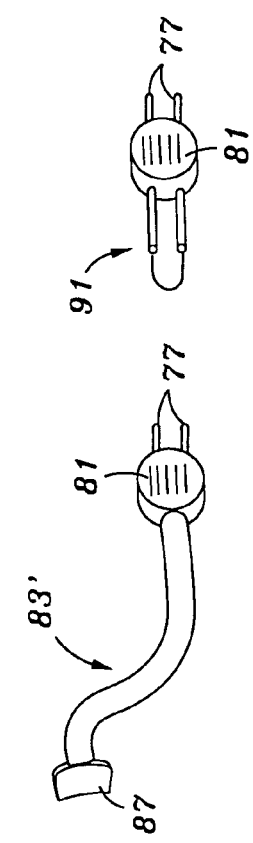

HEATING PEN, TACK SEATING DEVICE, AND TAP AND SURGICAL IMPLANTATION METHODS USING SAME

This application claims the benefit of U.S. Provisional Application No. 60/157,825, filed Oct. 5, 1999, the entire contents of which are expressly incorporated herein by reference.

BACKGROUND OF THE INVENTION

1. Field of the Invention

The present invention relates generally to medical devices and bio-resorbable plates and membranes and, more particularly, to tools for applying these plates and membranes to defected bone to splint, contain and provide support for the bone to heal.

2. Description of Related Art

A resorbable plate or membrane is typically manufactured with one or more apertures through which the surgeon can affix the plate or membrane to bone. A widely used technique for fixating a defected bone includes affixing a bio-resorbable internal fixation device over a defected bone segment or other bone defect to provide support while the bone defect heals. The internal fixation device, such as a plate or membrane, is affixed to the damaged bone about the bone defect. The bio-resorbable plate or membrane may be first heated, causing it to become malleable. Once malleable, the bio-resorbable plate or membrane is molded to conform to the contour of the bone area, and subsequently affixed over that area by, for example, screws to fixate the membrane to the bone. This general technique is set forth, for example, in Lemperle et al, U.S. Pat. No. 5,919,234 entitled RESORBABLE, MACRO-POROUS, NON-COLLAPSING AND FLEXIBLE MEMBRANE BARRIER FOR SKELETAL REPAIR AND REGENERATION, the entire contents of which are expressly incorporated herein by reference. During the application process the plate or membrane hardens as it cools, which may leave, for example, imperfectly seated portions of the plate or membrane that have been placed prior to the plate or membrane hardening. In some instances, the surgeon must then remove the membrane, heat it, and attempt to position the membrane over the bone defect once again. Moreover, additional time and inconvenience is required for the positioning and securing of the screws into the plates or membranes. Neuro-surgeons, for example, would generally prefer to not be bothered with threading of an aperture drilled in a bone via the use of a tapping device, with the positioning of a screw properly so that the threads are engaged but not crossed and, subsequently, with the threading of the screw into the threaded aperture to the proper tightness so that the screw is not too loose and yet is not damaged by over-tightening.

SUMMARY OF THE INVENTION

The present invention provides improved apparatus, systems, and methods for shaping and attaching bio-resorbable plates and membranes to bone defect areas. In accordance with one aspect of the present invention, a resorbable plate or membrane is submerged in a hot solution until it becomes malleable. Once malleable, the plate or membrane is molded to conform to the contours of the bone defect area, and subsequently fixed over that area. During the application process the plate or membrane hardens as it cools, which may leave, for example, imperfectly seated portions of the plate that have been placed prior to plate or membrane hardening. In accordance with one aspect therefore, the improved apparatus, systems and methods of the present invention advantageously allow the surgeon to further closely shape the plate or membrane to the contours of the bone, in vivo, once the plate or membrane cools and hardens after the initial shaping.

The in vivo molding or shaping of plates and membranes is accomplished with the use of a heating pen. The heating pen comprises a handle and a shaper. At the distal end of the handle is a nose, which includes two conductive apertures. The shaper comprises a pair of parallel conductive prongs that fit into the conductive apertures at the nose of the handle. The prongs are held together by a disk shaped housing. Opposite the prongs is an extender. At the tip of the extender is a heating metal pad, which is engineered to rapidly transfer heat to the material of the membrane or plate to thereby bring the material to its glass transition temperature, where the membrane or plate becomes malleable.

In use, the plate or membrane is first submerged in a heated solution until it reaches its glass transition temperature and becomes malleable. The plate or membrane is then placed over a bone defect, where it begins to harden as it cools. To maintain the malleability of the plate or membrane, the surgeon holds the heating pen and heats up the heating pad, which is preferably metal, by compressing an outwardly biased lever. Once the metal pad is heated, the surgeon directs the metal pad against the hardened plate or membrane in vivo to warm the plate or membrane, causing it to once again become malleable. In this manner the surgeon can further form the malleable plate or membrane onto the bone for a better fit, for example, by maneuvering and compressing the heated metal pad about the plate or membrane.

Additionally, the improved apparatus, systems and methods of the present invention allow the surgeon to fix the plate or membrane to the bone quickly and efficiently using tacks. One aspect of the present invention entails the use of a tack fastener and a tack seating device to conveniently and effectively place tacks through an internal fixation device and into the bone. In accordance with one aspect of the present invention, a tack seating device is provided for automatically seating the tacks into a bone hole prepared by the surgeon. Each tack is automatically seated with a driving force produced by the tack seating device to allow secure seating of the tack wherein the manual driving force for insertion of the tack is limited to a period of time on the order of about one second.

The fasteners used in accordance with one feature of the present invention are bio-resorbable tack fasteners. Bone screws are a second type of fastener. Each tack fastener comprises a head, a shaft and radial protrusions along the length of the shaft. The tack seating device is equipped with an end to receive the head of a tack. The tack is then automatically seated via a driving force by the tack seating device.

A cutting filament for cutting plates, tacks, screws, and other resorbable or plastic elements, may also be used with the heating pen. The heating pen allows the surgeon to cut away surplus portions of the plate, membrane, or other implants. Once the cutting filament is heated, the surgeon directs the filament against the plate, membrane, or other implant, in vivo, to cut the plate, membrane or implant. In this manner the surgeon can further form the plate, membrane, or other implant onto the bone for a better fit, for example, by removing surplus edges or material.

BRIEF DESCRIPTION OF THE DRAWINGS

FIG. 1A is a side view of the tack seating device of the present invention in the relaxed position.

FIG. 1B is a side view of the tack seating device of the present invention in the "cocking" position.

FIG. 1C is a side view of the trigger mechanism of the tack seating device of the present invention.

FIG. 2 is a side cross-sectional view of a tack fastener engaged with the tack seating device of the present invention, in the "cocked" position.

FIG. 3 is a side view of the trigger mechanism of the tack seating device of the present invention.

FIG. 6A is a side view of the trigger mechanism of the tack seating device of the present invention, in the relaxed position.

FIG. 6B is a side view of the trigger mechanism of the tack seating device of the present invention, in the "cocked" position.

FIGS. 7A–7E are side cross-sectional views of a tack fastener being used in conjunction with the tack seating device of the present invention.

FIG. 8A is a perspective view of the tack-fastener container of the present invention; FIG. 8B is a detailed cross-sectional view of the tack-fastener container and tack seating device in use.

FIG. 11 is a schematic side view of a tack fastener of the present invention.

FIG. 12A is a schematic side view of a tack of the present invention prior to insertion into a bone hole.

FIG. 12B is a schematic side view of the tack of FIG. 12A after being distorted by insertion into a bone hole.

FIG. 13 is a side view of the heating pen device of the present invention.

FIG. 14 is a side exploded view of the heating pen device of the present invention.

FIG. 15 is a side view of the heating pad portion with an extender for the heating pen device of the present invention.

FIG. 16 is a side view of a cutting filament for the heating pen device of the present invention.

FIG. 17 is a side view of the cap for the heating pen device of the present invention.

Figure 4:
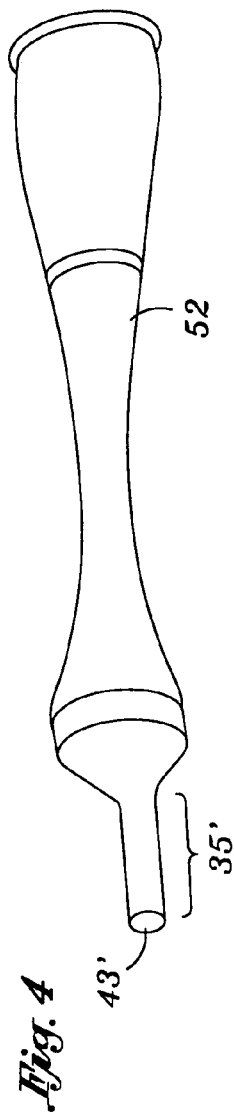
FIG. 4 is a side view of the embodiment of the present invention of a manual tack seating device of the present invention.

The present invention, together with additional features and advantages thereof, may best be understood by reference to the following description taken in connection with the accompanying illustrative drawings.

DETAILED DESCRIPTION OF THE DRAWINGS

Referring more particularly to the drawings, FIGS. 1A–1C illustrate a tack seating device 31 for automatically seating a tack fastener into a bone aperture. The tack seating device 31 is constructed to apply a single, predetermined driving force to the tack fastener to thereby quickly and consistently seat the tack fastener into a bone aperture. Thus, manual driving forces and periods of time greater than about a second are not required of the surgeon for seating each tack fastener.

The tack seating device 31 thus provides for a reliable and brisk entry of the tack fastener into the bone aperture, whereas manual seating devices may require iterative pressures or rotations, for example, to set each radial protrusion of the tack fastener into a bone aperture. The iterative pressing in such manual seating operations may create excessive pressure at the damaged bone area and cause collapse or undesired movements of the bone fragments. Moreover, the iterative pressing may damage the tack fastener. Tapping of bone apertures to receive screws can present similar problems.

In accordance with the present invention, the tack seating device is constructed and calibrated to provide a relatively precise driving pressure required for seating the tack fastener each time. The surgeon positions the tack fastener for seating and then activates the driving mechanism of the tack seating device. The tack seating device 31 preferably comprises a cylindrical housing 33 which includes a tack holder 35, a plunger 37 (FIGS. 6 and 7), a plunger spring 39 for driving the plunger 37, a tack-holder spring 51 for retracting the tack holder, and a trigger or release mechanism 41 for releasing the plunger spring. The tack holder distal end comprises a hollow cylindrical structure with an opening or mouth 43 at the tip. FIGS. 1A, 6A and 7A show the tack seating device in the relaxed position with the plunger 37 fully extended within the tack holder 35. As shown in FIGS. 1B, 7A, 7B and 7C, when pressure is applied to the tack holder distal end, both the tack holder 35 and the plunger 37 move and compress the plunger spring 39 and the tack-holder spring 51. The plunger 37 is thus moved proximally in a direction of the arrow A1 within the cylindrical housing 33, to a cocked position in which the lever 47 travels in a direction of the arrow A2, as shown in FIGS. 1B and 6B. The plunger 37 is retained in the cocked position by the pin 45 of the trigger or release mechanism 41, as shown in FIGS. 1C and 6B, but the tack holder 35 returns distally in a direction of the arrow A3 to its FIG. 1A position. The tack driving plunger 37 is released by the trigger or release mechanism 41 by depressing the lever 47, as shown by the arrow A4 in FIG. 1C.

Figure 5A:
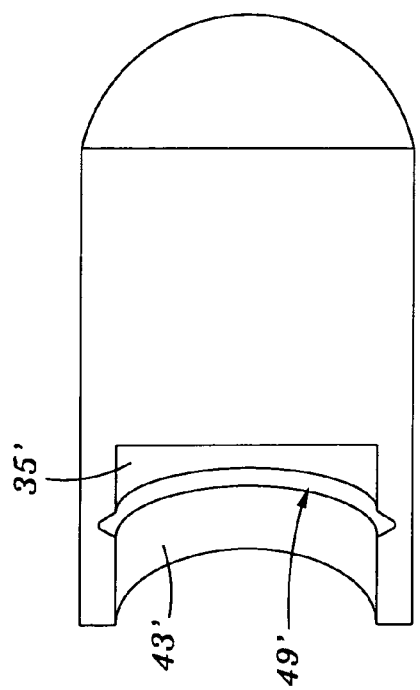
FIGS. 5A and 5B are side cross-sectional views of the grooved section of a manual embodiment of the tack seating device of the present invention.
Figure 5B:
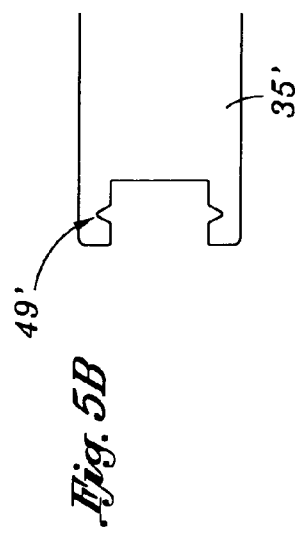

The opening or mouth 43 at the end of tack holder 35 is detailed in the embodiment illustrated in FIGS. 2 and 3. The mouth is formed with an internal radial groove 49 sized to be of slightly smaller diameter than the head of a given tack fastener. For example, as shown in FIGS. 2 and 3, the opening 43 can be optimally sized at about 3.98 mm for use with a tack fastener 50 having a tack-fastener head 50a diameter of about 4 mm, but other tolerances are possible. The diameter of the opening 43 is therefore slightly smaller than the diameter of a tack-fastener head. As such, the tack-holder opening stretches/deforms and/or the tack-fastener head compresses sufficiently to allow the enlarged-diameter portion of the tack-fastener head to slide into the interior of the tack holder 35. In the illustrated embodiment the radial groove 49 is of about 0.02 mm in depth, as is also shown in FIGS. 5A and 5B. Other groove depths or other tack holding structures may be incorporated so long as the tack fastener can be gripped and firmly held without substantial deformation of the tack fastener. The plunger 37 is preferably centrally coaxial to the tack holder 35, The tack holder 35 in this embodiment is actuated by the tack-holder spring 51, and the plunger 37 is actuated by the plunger spring 39. The radial groove 49 is preferably disposed near to the opening, so that shortly after the tack-fastener head penetrates the opening, it snaps into the radial groove 49, providing for a firm holding of the tack-fastener head, and thus the tack fastener 50.

In accordance with a modified embodiment of the present invention, a tack fastener may be seated within a manual tack seating device 52, as shown in FIG. 4. The manual tack seating device 52 is a simple mandrel that operates similarly to the tack fastener in loading and seating the tack fastener, but requires manual driving of the tack fastener into the bone aperture. As shown in FIGS. 5A and 5B the manual tack seating device embodiment similarly has a tack-holder end 35' with an opening or mouth 43' having a radial groove 49' to retain the end of a tack fastener. FIG. 5B shows a cross-sectional side view of the holder end 35'.

Referring now to FIGS. 6A and 6B the operation of the preferred embodiment of the trigger or release mechanism 41 of the tack seating device 31 of the present invention is illustrated. The plunger 37 is coaxially situated in the center of the hollow tack holder 35. The plunger 37 is coupled to plunger spring 39 and the tack holder 35 is coupled to a tack-holder spring 51. In the relaxed position, the springs 39 and 51 are uncompressed, and the distal ends of the plunger 37 and tack holder 35 protrude from the cylindrical housing 33. When axial external pressure is placed on the tip of the plunger 37 and the tack holder 35, the plunger 37 and tack holder 35 retract into the cylindrical housing 33 causing the respective springs 39 and 51 to which they are coupled to compress in the direction shown by arrow A1. The compressed plunger spring 39 that is coupled to the plunger 37 is eventually held in the compressed position while the tack-holder spring 51 that is coupled to the tack holder 35 is allowed to be moved into its decompressed position. Consequently, the compressed spring 39 to which the plunger is coupled, when decompressing, provides the driving force for the plunger 37 to move distally and drive the tack fastener into the bone aperture, with the proper amount of force for proper seating of the tack fastener.

Referring now to FIGS. 7A–7E and 8A–8B, in a preferred embodiment the axial pressures to compress the springs 39 and 51 are provided by the loading of the tack type of fastener 50. To load the tack fastener, the tack holder mouth 43 is axially pressed against the tack-fastener head as shown in 7A while the tack fastener is stored in a tack-fastener container 53 shown in FIG. 8A. The tack-fastener container serves as a stable support to position the tack fastener for it to be picked up by the tack seating device, by an assistant for example. The tapering from the top of the tack-fastener head allows the tack holder of the tack seating device to slide over the tack-fastener head with relative ease. The tapering from the lower surface allows for an adequate scaled space for the tack holder to completely envelop the tack-fastener head, wherein the tack-fastener head snaps into the radial groove, for a mechanical and audible positive feedback of proper operation. The axial compression of the tack holder against the tack-fastener head allows for the tack-fastener head to be picked up and also for the plunger to be cocked. Once cocked, the plunger can be released by the surgeon pressing on the other end of the lever to release the pin, to thus release the spring from compression. The released spring causes the plunger to move forward and drive the plunger axially against the tack-fastener head. The tapering on the lower surface of the tack-fastener head allows the tack-fastener head to smoothly slide out of the groove and into the bone aperture as the plunger presses against the tack-fastener head.

Once seated within the radial groove 49 of the tack holder, the tack-fastener head 50', detailed in FIGS. 7E and 8B, upon continued loading forces exerted by the surgeon, as shown in FIGS. 7A–7C, exerts pressure against an interior surface 55 (FIG. 8B) of the tack holder 35. The proximally directed pressure of the tack-fastener head 50' against the interior surface 55 forces the tack holder 35 to retract into the cylindrical housing against the bias of the tack-holder spring 51. As the tack-fastener head 50' presses against the interior flat surface 55 of the tack holder 35, it also comes into contact with the distal tip 85 of the plunger 37 and exerts proximal pressure against the plunger 37 causing the plunger 37 to retract against the bias of the plunger spring 39, as shown in FIGS. 7A–7C. This all preferably occurs in one fluid motion as the surgeon loads the tack fastener 50 from the tack-fastener container 53. In accordance with the presently preferred embodiment, both the tack holder 35 and the plunger 37 are separately spring loaded, and are both eventually loaded into a compressed position within the tack holder, as shown in FIG. 7C. The tack holder 35 is subsequently allowed to be moved into its decompressed position, as shown in FIGS. 6B and 7D.

Referring again to FIGS. 6A and 6B, the compressed plunger spring 39 and plunger 37 remain in a compressed (cocked) position by the trigger or release mechanism 41, while the tack holder 35 returns to the relaxed position. The shaft of the plunger 37 is one cylindrical unit having smaller 37a and larger 37b diameter segment, with the smaller diameter segment 37a protruding from the cylindrical housing 33. As such, there is effectively a step 37c from the larger diameter segment 37b to the smaller diameter segment 37a of the plunger shaft. The lever 41 rests on the exterior surface of the cylindrical housing 33 and extends axially along a portion of the length of the cylindrical housing 33. At a proximal end of the lever 41 is a pin 45, which extends into the cylindrical housing 33. In the relaxed position of FIG. 6A, the pin 45 exerts an inward force onto the larger diameter segment 37b under the influence of a lever spring 57 which is disposed between a distal end of the lever 41 and the exterior surface of the cylindrical housing 33. As shown in FIG. 6B, when the plunger 37 retracts proximally, the smaller diameter segment 37a of the plunger 37 moves toward the pin 45 in the direction of the arrow A1. Eventually, the pin 45 moves down the step 37c from the surface of the larger diameter segment 37b to the surface of the smaller diameter segment 37a of the plunger. As the lever spring 57 expands, the pin 45 drops to the smaller diameter segment 37a. The proximal side of the pin 45 will rests against the step 37c when the compressed plunger spring 39 is locked into the cocked position.

The trigger mechanism is released by removing the pin 45 from the step 37c by pressing the lever 71. When the pin 45 is removed from the step 37c, the plunger spring 39 decompresses and drives the plunger distally, hammering the tack fastener 50 out of the tack holder 35 and into the bone aperture. The tack seating device 31 of the present invention can thus almost instantaneously secured the tack fastener 50 into the pre-drilled bone aperture. As a result, a market advantage and reduction of the possibility of human error are present with the system and apparatus of the present invention. The neuro-surgeon, for example, can quickly drill an aperture that will subsequently receive a tack fastener which has been pre-seated within the tack seating device 31 by an assistant. The neuro-surgeon can thus orient the tack seating device 31 for seating the tack fastener 50, and press the trigger 41 to completely seat the tack fastener 50, allowing the surgeon to concentrate more of his or her on other surgical tasks.

Figure 9:
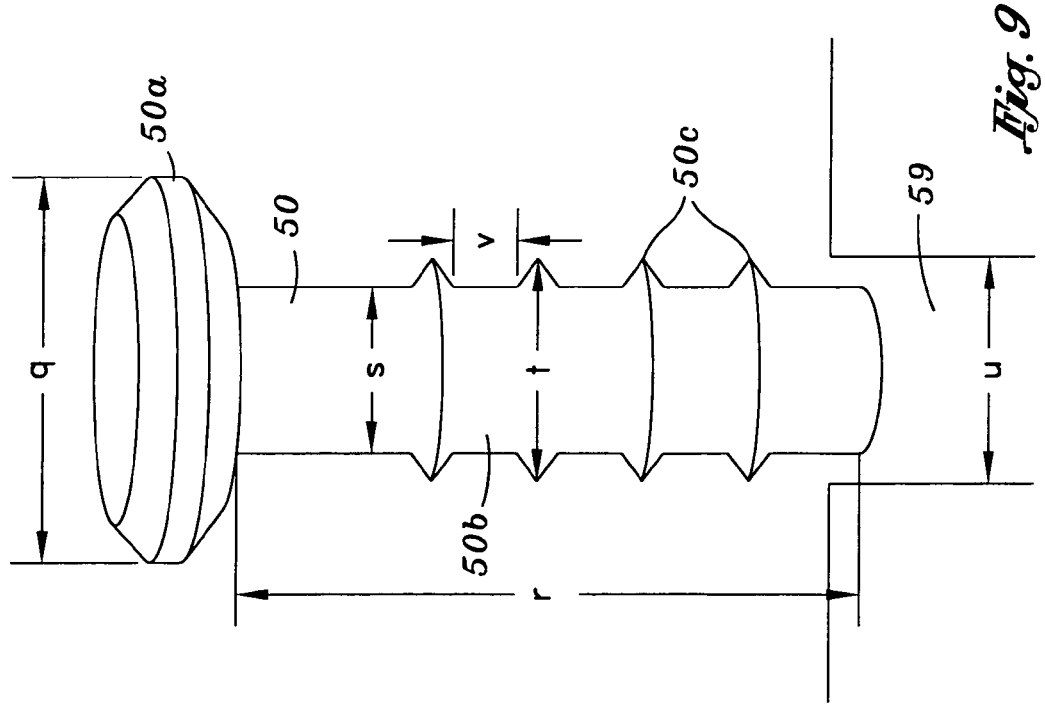
FIG. 9 is a side view of the tack fastener of the present invention.
Figure 18D:
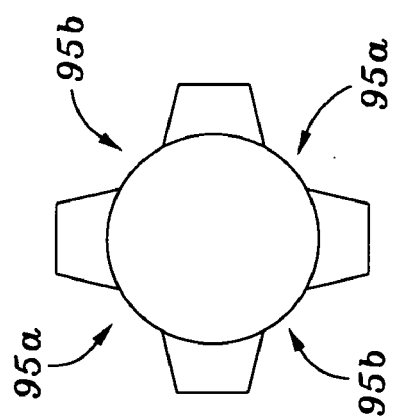
FIG. 18D is a top view of the fluted screw tap of FIG. 18-C.
Figure 18C:
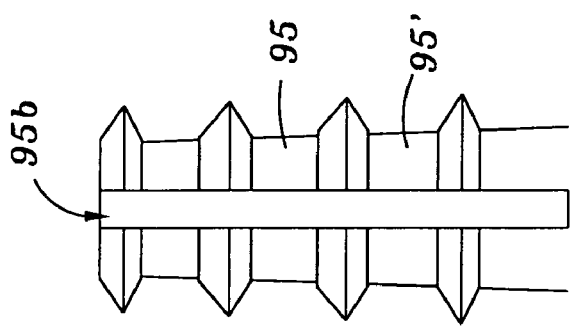
FIGS. 18A–C are side views of fluted screw taps in accordance with the the present invention.
Figure 18B:
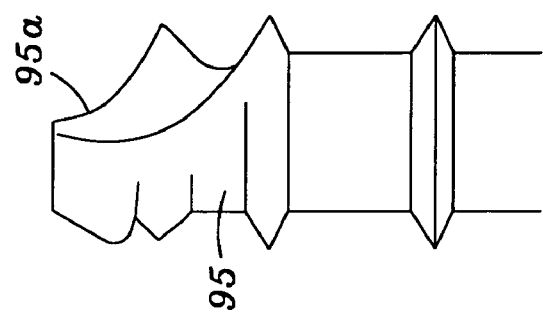
Figure 18A:
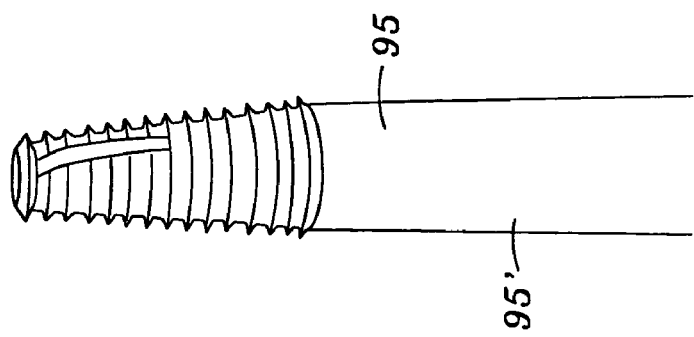

The fasteners used in accordance with one feature of the present invention are bio-resorbable tack fasteners. Referring now to FIG. 9 each tack fastener 50 comprises a head 50a, a shaft 50b and radial protrusions 50c along the length of the shaft. The tack fastener used in one illustrated embodiment has a head diameter of 4.0 mm (shown at q), a shaft length of 4 to 6 mm (shown at r), a shaft minor diameter of 1.4 mm (shown at s), and a shaft major diameter of 1.7 mm (shown at t), for a bone aperture of 1.5 mm in diameter (shown at u). The radial protrusions 50c are spaced from point to point at a distance of about 0.6 mm (shown at v). The illustrated tack fastener has four radial protrusions which are preferably annular. The radial protrusions are designed to deformed 5 to 15 percent in the illustrated embodiment, to allow for the tack fastener to snugly fit in the pre-drilled bone aperture 59, which has a diameter of 1.5 mm. In modified embodiments, other scales, configurations, numbers of protrusions, and deformation percentages may be used.

Figure 10:
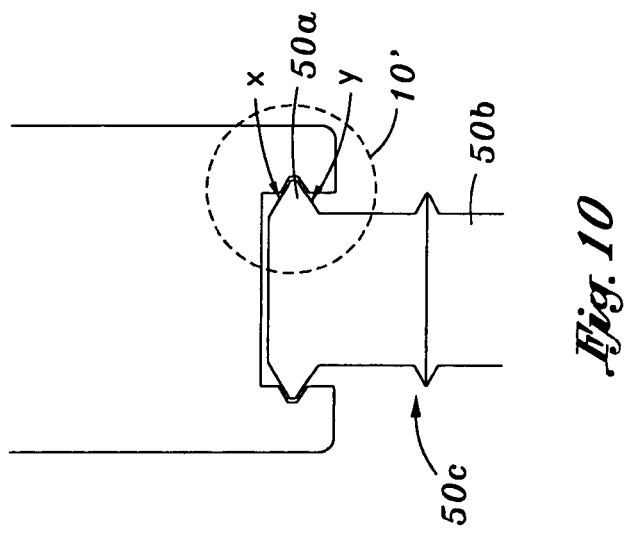
FIG. 10 is a detailed side view of the tack fastener being engaged by the tack seating device of the present invention.

In a preferred embodiment of the invention, shown in FIG. 10, the head 50a of the tack fastener 50 is tapered off at an angle from the top surface x and tapered from the lower surface y, providing for the outer peripheral edge of the head to be thinner than its center portions thereof, measured in a direction parallel to the tack axis. The radial protrusions 50c on the shaft 50b in the illustrated embodiment are symmetrically angled from the top surface and the lower surface. In accordance with other embodiments of the present invention, the peripheral edge of the head 50a may be rounded, providing for the outer peripheral of the head to be thinner than center portions; the radial protrusion may be angled from the lower surface only to form barbs; or there may be more or fewer radial protrusions on the shaft.

Another illustrated dimensional configuration is shown in FIG. 11, wherein the tack fastener comprises a shaft 50b with a length of about 2.5 mm, shown at y, and a pointed tack-fastener tip 50d. The radial protrusions 50c of this exemplary tack fastener have a major diameter of about 0.9 mm, shown at v, and a shaft minor diameter of about 0.8 mm, shown at w. The major diameters of the radial protrusions are spaced about 0.5 mm apart, shown at u, and the tack-fastener head 50a, shown at x, has a diameter of about 2.25 mm.

FIGS. 12A and 12B show the distorting effect that insertion into a bone aperture has on the radial protrusions of an exemplary tack fastener 50. In particular, FIG. 12A shows the dimensions of a bone screw prior to insertion, and FIG. 12B shows the effect on the tack fastener after compression into a bone aperture. The tack fastener has a shaft 50b minor diameter of about 1.2 mm both before and after compression, shown at u' and u. The distance between the radial protrusions is also the same before and after compression, about 0.5 mm, shown at w' and w. The radial protrusions 50c, however, have been inelastically distorted after tack-fastener insertion into a bone aperture, as shown in FIG. 12B. The major diameter of the radial protrusions have been reduced from about 1.5 mm, shown as v' in FIG. 12A, to only about 1.35 mm, shown at v in FIG. 12B, for an overall loss of major diameter of about nine percent. The contact area between the tack fastener and the wall of the bone aperture is thus increased, due to the flattening of the radial protrusion, as shown at z' and z, strengthening the tack fastener's purchase on the bone aperture.

In accordance with another aspect of the present invention, a heating pen apparatus is used for in vivo molding of plates and membranes. Referring to FIGS. 13–17, the heating pen 61 in the illustrated embodiment comprises a handle 63 and a shaper 65. The handle 63 is preferably tubular, with an interior battery compartment 67. On the proximal end of the handle is an insertion slot for batteries 69. On the surface and close to the distal end of the handle is a lever 71, biased outwardly. At the distal end of the handle is a nose 73. The nose has two conductive apertures 75. The shaper 65 comprises a pair of parallel conductive prongs 77 that fit into the conductive apertures 79 at the nose 73 of the handle. The prongs are held together by a disk shaped housing 81. Opposite the prongs is an extender 83, and at the tip of the extender is a heating pad 87, which as presently embodied comprises metal. The heating pad is engineered to rapidly transfer heat to the material of the membrane or plate to thereby bring the material to its glass transition temperature. Once brought to its glass transition temperature, the membrane or plate will become malleable.

In accordance with a method of the present invention, the plate or membrane is first heated to its glass transition temperature by submersion into a heated solution, and then placed ono bone. The heated solution preferably comprises a saline solution, but alternatively may comprise any biocompatable fluid suitable for heating resorbable plastics. After the plate or membrane has been placed and shaped, it will begin to cool and harden, The surgeon can then activate the heating pen 61 to heat the heating pad by compressing on the outwardly biased lever 71. Once the metal pad is heated, the surgeon directs the metal pad against the hardened plate or membrane in vivo, to further heat and form the plate or membrane onto the bone. The heated metal pad will cause the hardened area of the plate or membrane to become malleable. Once malleable, the surgeon can shape the plate or membrane, for example, by maneuvering and compressing the heated metal pad about the plate or membrane. The shaper 65 may alternatively be formed with a longer extender 83' to allow easier access to a plate or membrane by the surgeon, as shown in FIG. 15. The electricity for the heating pen may alternatively be supplied by standard 120 volt/60 Hz AC utility wall socket after being appropriately transformed to a safely lowered voltage.

There is shown in FIG. 16 a cutting filament 91 for cutting plates that may also be used with the heating pen in place of the shaper 65, also having parallel conductive prongs that fit into the conductive apertures of the heating pen in the same manner as the shaper. With this attachment the heating pen 61 allows the surgeon to cut away surplus portions of the plate, membrane, tack, screw or other elements. Once the cutting filament is heated, the surgeon directs the filament against the hardened plate or membrane in vivo to cut the plate, membrane, fastener or other plastic element. In this manner the surgeon can further form the plate or membrane onto the bone for a better fit, for example, by removing surplus edges. Additionally, the head or heads of tack or screws may be cut off for removal of a plate or membrane. The cutting filament may also be used, for example, to remove the portion of a misplaced tack fastener protruding from a misplaced bone aperture. A cap 93 is provided for the heating pen 61 that is large enough to allow storage with the shaper or filament attachment attached. The cap comprises slot 93' to allow the cap to pass about the outwardly biased lever when seated.

In practice, the bio-resorbable plate or membrane, the heating pen, tack fastener, tack-fastener container, and the tack-fastener seating device work together as a system.

Generally, the plate or membrane is submerged into a hot solution (saline water, for example) to become malleable. Once malleable, the plate or membrane is shaped to the contour of the bone area to be covered. The shaped plate or membrane can then in one embodiment be tacked to the bone surface. The molding of the plate or membrane and the insertion of tacks or screws may be an iterative procedure. For example, the surgeon inserts one tack fastener through a membrane with the tack seating device 31, molds the membrane in vivo with the shaper 65 of the heating pen 61, inserts another tack fastener with the tack seating device 31, performs additional molding with the shaper 65, inserts another two or more tack fasteners with the tack seating device 31, further molds the membrane with the shaper 65, inserts additional tack fasteners with the tack seating device, and removes unwanted portions of the membrane with the heating filament 91 of heating pen 61. The tack fasteners to be used are held and removed, for example, in the tack-fastener container 53 of the type and in the way as set forth above.

In certain instances, the surgeon may want to use an alternative fastener, for example, a screw. In this particular instance, the apertures in the bone will need to be tapped. The new apparatus for tapping the bone apertures provides for optimal threading of the aperture. A traditional problem of tapping is that too much bone debris may be left in the bone aperture. The bone debris can clog the aperture and/or effectively strip the thread inside the aperture. The present invention addresses this problem.

Referring now to FIGS. 18A–18D, in a preferred embodiment, the tap 95 has two short flutes 95a and two long flutes 95b. The relatively extensive fluting of the tap of the present invention allows for additional void volume between the bone and the tap. This additional void volume can better collect the bone debris, and thus efficiently remove them from the aperture. Although four long flutes would provide more space for bone debris to be collected, it has been discovered that the alternating short and long flutes of the present invention provide better performance with sufficient void volume and adequate structural strength/integrity of the shaft 95' of the tap.

As a modification to the method set forth above, resorbable screws may be used in addition to or as an alternative to the tack fasteners. The method would otherwise be similar, except for the fact that drilled apertures must be tapped. The tapping device of FIGS. 18A–D may be used, or a conventional tap used, in accordance with the present invention. A bio-resorbable plate or membrane is placed in hot water to bring it to glass transition temperature, making the plate or membrane malleable and pliable. The plate or membrane is placed over the bone defect area and shaped appropriately. The bone apertures where the tack fasteners and/or screws are to be inserted can be drilled and/or tapped, either before or after the plate or membrane is placed over the bone area, or iteratively. For example, an aperture is drilled and tapped, one screw is placed through a membrane, the plate or membrane is molded with the heat pen, another tack fastener or screw is placed, additional molding with the heat pen occurs, etc. The heated water bath, heating pen, tack seating device, and tap, can thus be used throughout the implantation process.

The aforesaid detailed description, and the figures to which it refers, are provided for the purpose of describing examples and specific embodiments of the invention only and are not intended to exhaustively describe all possible examples and embodiments of the invention. Many other changes, modifications and substitutions, in addition to those set forth in the above paragraphs, may be made by one having ordinary skill in the art without necessarily departing from the spirit and scope of the present invention.

The invention claimed is:

1. A method for affixing a bone plate or membrane to a bone comprising:
    a) drilling an aperture in a bone;
    b) placing a bone plate or membrane in hot solution to bring it to glass transition temperature;
    c) locating or creating a hole in the bone plate or membrane;
    d) aligning the aperture in the bone plate or membrane with the aperture in the bone;
    e) loading a tack seating device with a tack fastener, wherein the tack seating device comprises a member having a handle end and a tack holder distal end that includes a portion with an internal radial groove sized to receive the head of the tack fastener and loading is achieved by seating the head of a tack fastener within the internal groove to occlude the tack holder; and
    f) inserting the tack fastener through the aperture in the bone plate or membrane and the aperture in the bone with the tack seating device.

2. The method for affixing a bone plate or membrane to a bone of claim 1, wherein the tack seating device includes:
    a) a handle having a tack holder distal end;
    b) a plunger actuated by a plunger spring—within the handle, the plunger being movable from a relaxed position to a cocked position wherein the plunger spring is compressed; and
    c) a retaining mechanism to retain the plunger in the cocked position and further to release the plunger and cause the plunger to contact the tack fastener and move it into the bone aperture.

3. The method for affixing a bone plate or membrane to a bone of claim 2, and further including:
    a) providing a heating pen, the heating pen including a switch which is in electrical communication with an electric power source, and further including a heating pad which is in electrical communication with the switch;
    b) heating the heating pad by passing electrical current from the switch to the heating pad;
    c) placing the heating pad in contact with a portion of the bone plate or membrane to thereby bring the bone plate or membrane to its glass transition temperature;
    d) bending or shaping the heated bone plate or membrane portion to conform to the contour of the bone.

4. The method for affixing a bone plate or membrane to a bone of claim 2, and further including:
    a) providing a heating pen having a handle with a switch for providing electrical power to a filament—affixed to the handle;
    c) heating with the filament a portion of the bone plate or membrane to its glass transition temperature;
    d) cutting a portion of the plate or membrane with the filament of the cutting filament.

5. A method for—shaping or forming a bone plate or membrane in vivo, comprising:
    a) applying a bone plate or membrane that becomes malleable at a glass transition temperature to a bone;
    b) providing a heating pen having a handle with a switch for providing electrical power to a heating pad, which is affixed via an extender to a distal end of the handle and which comprises a contacting surface with an enlarged width, measured in a direction transverse to a longitudinal axis of the extender, relative to a corresponding reduced width of the extender, that is constructed to contact and apply heat to a bone plate or membrane;

c) heating with the heating pad a portion of the bone plate or membrane to its glass transition temperature, while the bone plate or membrane is within a patient; and d) bending or shaping the heated bone plate or membrane portion to conform to the contour of the bone.

6. The method for shaping or forming a bone plate or membrane in vivo of claim 5, and further including:

a) providing a heating pen having a handle with a switch for providing electrical power to a filament affixed to the handle;

c) heating with the filament a portion of the bone plate or membrane to its glass transition temperature; and d) cutting a portion of the plate or membrane or of the tack fastener applied to the bone with the filament.

7. The method of claim 5, wherein the providing comprises providing a heating pad with a contacting surface having a cross-sectional area that is greater than a cross-sectional area of the extender.

8. The method of claim 5, wherein the providing comprises providing a heating pad with a contacting surface having a cross-sectional area that is greater than a cross-sectional area of the extender at a point where the heating pad is affixed.

9. The method of claim 5, wherein the providing comprises providing a heating pad with a contacting surface having a cross-sectional area that is greater than a cross-sectional area of the extender, the cross-sectional areas being measured in a direction transverse to a longitudinal axis of the heating pen.

10. The method of claim 5, wherein:

the handle comprises a proximal portion, a distal portion to which the heating pad is affixed, and an axis extending between the proximal portion and the distal portion; and the providing comprises providing a heating pad with a cross-sectional area that is greater than a cross-sectional area of the extender, the cross-sectional areas being measured in a direction transverse to the axis.

11. A system for applying a bone plate or membrane to a bone, comprising:

a) a tack seating device including a handle member having a handle end and a tack holder distal end, the tack holder distal end having a portion with an internal radial groove sized to receive the head of a tack fastener and further including a trigger or retaining mechanism to retain a plunger in a cocked position and further to release the plunger and cause it to contact the tack fastener and move it distally out of the internal radial groove and into the bone;

b) a heating pen for shaping or forming a bone plate or membrane in vivo, including a handle member having a nose end with conductive members and a switch to control the flow of electricity to the conductive members;

c) a shaper affixable to the heating pen and having conductive elements and a heating pad in electrical communication with the conductive elements, wherein when affixed to the nose end of the heating pen the shaper can be heated by way of the conductive members and conductive elements sufficiently to enable the shaper to bring a bone plate or membrane to its glass transition temperature; and d) a cutting filament affixable to the heating pen and having conductors, wherein when affixed to the nose end of the heating pen the cutting filament can be heated by way of the conductive members and conductors sufficiently to enable the cutting filament to cut through a resorbable bone plate or membrane.

12. A beating pen for shaping or forming a bone plate or membrane in vivo, comprising:

a) a handle member having a nose end with conductive members and a switch to control the flow of electricity to the conductive members; and b) a shaper having a heating pad and an extender affixable to the nose end of the handle member so that conductive elements are in electrical communication with the conductive members, a distal tip of the heating pad having a first cross-sectional area that is greater than a second cross-sectional area of the extender and the heating pad being capable of heating to and remaining at a temperature suitable to bring a resorbable bone plate or membrane to its glass transition temperature.

13. The heating pen for shaping or forming a bone plate or membrane in vivo of claim 12, further comprising—a cutting filament having a filament affixable to the nose end of the handle member so that the conductive elements are in electrical communication with the conductive members, wherein the filament will beat to a temperature sufficient to cut through a resorbable bone plate or membrane.

14. The heating pen for shaping or forming a bone plate or membrane in vivo of claim 12, wherein the heating pad comprises a non-convex contacting surface constructed to contact and apply heat to a bone plate or membrane.

15. The heating pen for shaping or forming a bone plate or membrane in vivo of claim 14, the cross-sectional areas being measured in a direction transverse to a longitudinal axis of the heating pen.

16. The beating pen for shaping or forming a bone plate or membrane in vivo of claim 12, wherein the heating pad has a contacting surface with a cross-sectional area that is greater than a cross-sectional area of the extender.

17. A tack fastener device for affixing a bone or plate to bone, comprising a member having a handle end and a tack holder distal end that includes a portion with an internal radial groove sized to receive and hold a head of the tack fastener and further comprising a plunger that can be actuated to contact a proximal part of the tack fastener and drive it distally out of the internal radial groove and into the bone wherein:

the plunger can be actuated by a plunger spring that can be moved from a relaxed position to a cocked position wherein the plunger compresses the plunger spring; and the tack fastener device further comprises a trigger or retaining mechanism to retain the plunger in the cocked position and further to release the plunger and cause it to contact the tack fastener and move it outwardly.

18. The tack fastener of claim 17, wherein the tack holder distal end is biased by a tack holder spring and is constructed to move coaxially with the plunger from an unbiased position to a biased position.

19. The tack fastener of claim 18, wherein the tack holder distal end moves to the biased position while the plunger is being moved from a relaxed position to a cocked position, and then returns to an unbiased position while leaving the plunger in the cocked position.

20. A tack fastener device for affixing a bone or plate to bone, comprising:
- a plunger actuated by a plunger spring that can be moved from a relaxed position to a cocked position wherein the plunger compresses the plunger spring;
- a member having a handle end and a tack holder distal end that includes a portion with an internal radial groove sized to receive and hold a head of the tack fastener, the tack holder distal end being biased by a tack holder spring and being constructed to move coaxially with the plunger from an unbiased position to a biased position; and
- a trigger or retaining mechanism to retain the plunger in the cocked position and further to release the plunger and cause it to contact the tack fastener and move it outwardly.

21. The tack fastener of claim 20, wherein the tack holder distal end moves to the biased position while the plunger is being moved from a relaxed position to a cocked position, and then returns to an unbiased position while leaving the plunger in the cocked position.

22. A method for shaping or forming a bone plate or membrane in vivo, comprising:
- a) applying a bone plate or membrane that becomes malleable at a glass transition temperature to a bone;
- b) providing a heating pen having a handle with a switch for providing electrical power via an extender to a heating pad, wherein the extender is affixed to an affixation part at a distal end of the handle and the heating pad has a first cross-sectional area that is greater than a second cross-sectional area of the extender;
- c) heating with the heating pad a portion of the bone plate or membrane to its glass transition temperature, while the bone plate or membrane is within a patient; and
- d) bending or shaping the heated bone plate or membrane portion to conform to the contour of the bone.

23. The method of claim 22, wherein the providing comprises providing a heating pad with a contacting surface having a cross-sectional area that is greater than the second cross-sectional area.

24. The method of claim 22, wherein the providing comprises providing a heating pad with the first cross-sectional area being greater than the second cross-sectional area, the cross-sectional areas being measured in a direction transverse to a longitudinal axis of the heating pen.

25. The method of claim 24, wherein:
- the providing comprises providing a handle having a proximal portion and a distal portion that includes the affixation part; and
- the longitudinal axis extends between the proximal portion and the distal portion.

* * * * *